(12) United States Patent
Druma et al.

(10) Patent No.: US 10,405,907 B2
(45) Date of Patent: Sep. 10, 2019

(54) LOW COST LOW PROFILE INFLATABLE BONE TAMP

(71) Applicant: Medtronic Holding Company Sàrl, Tolochenaz (CH)

(72) Inventors: Calin Druma, San Jose, CA (US); Bruce Chabansky, Palo Alto, CA (US)

(73) Assignee: Medtronic Holding Company Sàrl, Tolochenaz (CH)

( * ) Notice: Subject to any disclaimer, the term of this patent is extended or adjusted under 35 U.S.C. 154(b) by 0 days.

(21) Appl. No.: 15/398,402

(22) Filed: Jan. 4, 2017

(65) Prior Publication Data

US 2017/0112556 A1    Apr. 27, 2017

Related U.S. Application Data

(63) Continuation of application No. 13/082,781, filed on Apr. 8, 2011, now Pat. No. 9,554,840.

(51) Int. Cl.
| | |
|---|---|
| A61B 17/70 | (2006.01) |
| A61B 17/88 | (2006.01) |
| A61B 90/00 | (2016.01) |
| A61B 17/00 | (2006.01) |
| A61B 17/32 | (2006.01) |

(52) U.S. Cl.
CPC .... *A61B 17/8855* (2013.01); *A61B 17/00234* (2013.01); *A61B 17/8822* (2013.01); *A61B 90/39* (2016.02); *A61B 2017/320048* (2013.01); *A61B 2090/3966* (2016.02)

(58) Field of Classification Search
CPC . A61B 5/6853; A61B 17/885; A61B 17/8852; A61B 17/8855; A61B 17/8858; A61M 25/002; A61M 25/0023; A61M 25/0017; A61M 25/104; A61M 25/00; A61M 25/10; A61F 2/958
USPC ............. 606/79–86 R, 99, 191–196, 108; 604/544, 96.01
See application file for complete search history.

(56) References Cited

U.S. PATENT DOCUMENTS

| | | | |
|---|---|---|---|
| 4,646,742 A * | 3/1987 | Packard | A61M 25/1018 604/102.02 |
| 4,819,751 A | 4/1989 | Shimada et al. | |
| 5,030,227 A | 7/1991 | Rosenbluth et al. | |
| 5,267,959 A | 12/1993 | Forman | |
| 5,328,468 A | 7/1994 | Kaneko et al. | |
| 5,348,537 A * | 9/1994 | Wiesner | A61M 25/0075 604/103.1 |
| 5,522,800 A | 6/1996 | Crocker | |
| 5,531,689 A * | 7/1996 | Burns | A61M 25/0075 604/99.04 |
| 5,649,908 A | 7/1997 | Itoh | |
| 5,843,116 A * | 12/1998 | Crocker | A61M 25/1002 606/192 |
| 5,948,345 A | 9/1999 | Patel et al. | |

(Continued)

*Primary Examiner* — Zade Coley
*Assistant Examiner* — Jessica Weiss

(57) ABSTRACT

An inflatable bone tamp for performing a minimally invasive surgical procedure includes a shaft having a primary region and a reduced diameter region, and an inflatable structure surrounding at least a portion of the reduced diameter region. The reduced diameter region of the shaft allows the deflated size of the inflatable structure to be minimized, while at the same time eliminating the need for the conventional dual lumen balloon catheter construction.

20 Claims, 9 Drawing Sheets

(56) References Cited

U.S. PATENT DOCUMENTS

| | | | |
|---|---|---|---|
| 6,231,543 B1 * | 5/2001 | Hegde | A61M 25/10 604/96.01 |
| 6,537,480 B1 | 3/2003 | Becker et al. | |
| 6,579,484 B1 | 6/2003 | Tiernan et al. | |
| 6,648,854 B1 * | 11/2003 | Patterson | A61M 25/005 604/524 |
| 6,740,107 B2 * | 5/2004 | Loeb | A61B 18/24 606/13 |
| 6,740,191 B2 | 5/2004 | Clarke et al. | |
| 6,837,871 B2 | 1/2005 | Gonzales et al. | |
| 6,902,571 B2 | 6/2005 | Owens et al. | |
| 6,960,188 B2 * | 11/2005 | Jorgensen | A61M 25/1006 604/103.09 |
| 7,025,745 B2 | 4/2006 | Lim et al. | |
| 7,220,336 B2 | 5/2007 | Flanagan | |
| 7,261,850 B2 | 8/2007 | van Ockenburg et al. | |
| 7,637,886 B2 | 12/2009 | Herweck et al. | |
| 7,820,936 B2 | 10/2010 | Weber et al. | |
| 7,862,541 B2 | 1/2011 | Jeffrey et al. | |
| 2001/0039411 A1 * | 11/2001 | Johansson | A61B 5/14539 604/509 |
| 2006/0004457 A1 * | 1/2006 | Collins | A61M 29/02 623/17.16 |
| 2008/0004568 A1 * | 1/2008 | Jeffrey | A61M 25/0069 604/96.01 |
| 2011/0106007 A1 * | 5/2011 | Auyoung | A61B 17/8822 604/96.01 |

\* cited by examiner

LOW COST LOW PROFILE INFLATABLE BONE TAMP

CROSS REFERENCE TO RELATED APPLICATIONS

This application is a continuation of U.S. Patent application Ser. No. 13/082,781, filed on Apr. 8, 2011, which is expressly incorporated herein by reference, in its entirety.

FIELD OF THE INVENTION

The invention relates to a system and method for performing a surgical procedure, and in particular, to an inflatable device that incorporates a catheter with a reduced diameter distal region for improved manufacturability.

BACKGROUND OF THE INVENTION

A minimally invasive procedure is a medical procedure that is performed through the skin or an anatomical opening. In contrast to an open procedure for the same purpose, a minimally invasive procedure will generally be less traumatic to the patient and result in a reduced recovery period.

However, there are numerous challenges that minimally invasive procedures present. For example, minimally invasive procedures are typically more time-consuming than their open procedure analogues due to the challenges of working within a constrained operative pathway. In addition, without direct visual feedback into the operative location, accurately selecting, sizing, placing, and/or applying minimally invasive surgical instruments and/or treatment materials/devices can be difficult.

For example, for many individuals in our aging world population, undiagnosed and/or untreatable bone strength losses have weakened these individuals' bones to a point that even normal daily activities pose a significant threat of fracture. In one common scenario, when the bones of the spine are sufficiently weakened, the compressive forces in the spine can cause fracture and/or deformation of the vertebral bodies. For sufficiently weakened bone, even normal daily activities like walking down steps or carrying groceries can cause a collapse of one or more spinal bones. A fracture of the vertebral body in this manner is typically referred to as a vertebral compression fracture. Other commonly occurring fractures resulting from weakened bones can include hip, wrist, knee and ankle fractures, to name a few.

Fractures such as vertebral compression fractures often result in episodes of pain that are chronic and intense. Aside from the pain caused by the fracture itself, the involvement of the spinal column can result in pinched and/or damaged nerves, causing paralysis, loss of function, and intense pain which radiates throughout the patient's body. Even where nerves are not affected, however, the intense pain associated with all types of fractures is debilitating, resulting in a great deal of stress, impaired mobility and other long-term consequences. For example, progressive spinal fractures can, over time, cause serious deformation of the spine ("kyphosis"), giving an individual a hunched-back appearance, and can also result in significantly reduced lung capacity and increased mortality.

Because patients with these problems are typically older, and often suffer from various other significant health complications, many of these individuals are unable to tolerate invasive surgery. Therefore, in an effort to more effectively and directly treat vertebral compression fractures, minimally invasive techniques such as, vertebroplasty and, subsequently, kyphoplasty, have been developed. Vertebroplasty involves the injection of a flowable reinforcing material, usually polymethylmethacrylate (PMMA—commonly known as bone cement), into a fractured, weakened, or diseased vertebral body. Shortly after injection, the liquid filling material hardens or polymerizes, desirably supporting the vertebral body internally, alleviating pain and preventing further collapse of the injected vertebral body.

Because the liquid bone cement naturally follows the path of least resistance within bone, and because the small-diameter needles used to deliver bone cement in vertebroplasty procedure require either high delivery pressures and/or less viscous bone cements, ensuring that the bone cement remains within the already compromised vertebral body is a significant concern in vertebroplasty procedures. Kyphoplasty addresses this issue by first creating a cavity within the vertebral body (e.g., with an inflatable balloon) and then filling that cavity with bone filler material. The cavity provides a natural containment region that minimizes the risk of bone filler material escape from the vertebral body. An additional benefit of kyphoplasty is that the creation of the cavity can also restore the original height of the vertebral body, further enhancing the benefit of the procedure.

Conventional inflatable bone tamps (IBTs) used in kyphoplasty procedures incorporate a "dual lumen" construction, in which a balloon is connected between distal tips of coaxial catheters, such that an inflation path for the balloon is defined between the coaxial catheters. However, in many instances, it can be desirable to reduce the production and manufacturing complexity associated with the assembly of this conventional dual lumen IBT construction.

Accordingly, it is desirable to provide an IBT that can be reduce manufacturing costs and complexity.

SUMMARY OF THE INVENTION

By providing a bone tamp with an inflatable structure having an expansion profile that exhibits greater distal expansion than proximal expansion (i.e., outwardly tapering), a kyphoplasty procedure can be performed in which lifting forces are more effectively applied to the endplates of a collapsed vertebral body, thereby enhancing the likelihood of height restoration of the vertebral body during the procedure.

As used herein, "expansion profile" refers to the shape of an inflatable structure during elastic expansion of the structure (i.e., expansion beyond the inflated, non-distended state of the structure). Furthermore, "outwardly tapering" refers to a state in which a maximum dimension (e.g., radial diameter, radial width or height) of a proximal half of the inflatable structure is less than a maximum dimension of a distal half of the inflatable structure.

In one embodiment, an inflatable bone tamp can include an inflatable structure formed from multiple curved lobes, such as a proximal lobe and a distal lobe. By sizing the distal lobe(s) to have a larger maximum non-distended radial diameter larger than a maximum non-distended radial diameter of the proximal lobe(s), the inflatable structure will exhibit an outwardly tapering profile when inflated.

In various other embodiments, an outwardly tapering inflation profile can be incorporated into an inflatable structure via features on the surface of an inflatable element (e.g., regions of additional material such as strips or bands), features within an inflatable element (e.g., internal webbing or straps), wall thickness variations in an inflatable element, or even external restraints that fit over an inflatable element (e.g., stents, sleeves, or strings).

In another embodiment, a surgical system for treating bone can include one or more inflatable bone tamps exhibiting outwardly tapering inflation profiles. The surgical system can further include additional equipment for performing a surgical procedure (e.g., one or more cannulas sized to accept the inflatable bone tamps, access tools such as drills, guide wires, obturators, trocars, and/or curettes) and/or instructions for performing the surgical procedure using the one or more inflatable bone tamps.

In various other embodiments, a surgical procedure such as kyphoplasty can be performed by creating an access path using a cannula, inserting an inflatable bone tamp having an outwardly tapering inflation profile into a target bone (e.g., a fractured vertebra) via the cannula, inflating the bone tamp to create a cavity in cancellous bone and restore the original cortical bone profile (e.g., restore vertebral body height), deflating and removing the inflatable bone tamp, and then filling the cavity with bone filler material to support the treated bone.

In a procedure such as kyphoplasty, the outwardly tapering expansion profile of the inflatable bone tamp allows the inflation force of the bone tamp to be more effectively directed towards the endplates of the fractured vertebra. This in turn enhances the ability of the bone tamp to restore the height of the vertebra, rather than simply compacting a larger portion of cancellous bone within the vertebra.

As will be realized by those of skilled in the art, many different embodiments of an inflatable bone tamp exhibiting an outwardly tapering expansion profile, systems, kits, and/or methods of using such an inflatable bone tamp according to the present invention are possible. Additional uses, advantages, and features of the invention are set forth in the illustrative embodiments discussed in the detailed description herein and will become more apparent to those skilled in the art upon examination of the following.

DETAILED DESCRIPTION

By incorporating a catheter having a reduced-diameter distal region into an inflatable bone tamp (IBT), the cost associated with manufacturing the IBT may be significantly reduced while still maintaining IBT performance.

Figure 1A:
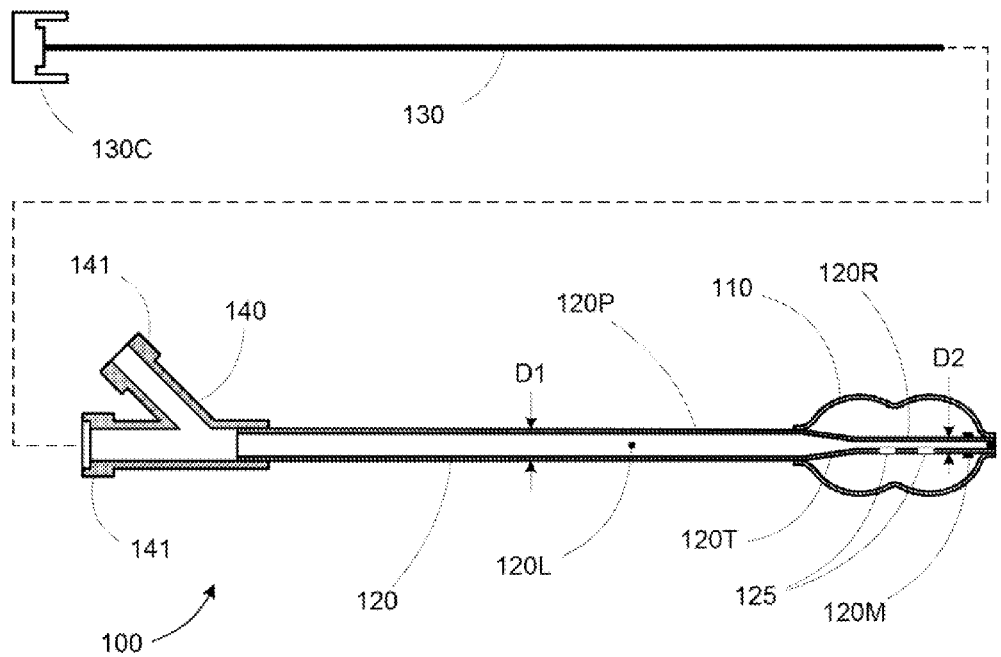
FIGS. 1A-1B show an exemplary inflatable bone tamp that incorporates a single catheter having a reduced-diameter distal region.

FIG. 1A shows an embodiment of an inflatable bone tamp 100 that includes a shaft 120 (e.g., a catheter), an inflatable structure 110 (e.g., a balloon) at the distal end of shaft 120, and a connector 140 (e.g., a Luer Lock fitting) at the proximal end of shaft 120. Note that while connector 140 is depicted as a "Y" connector (i.e., two fittings or ports) for exemplary purposes, connector 140 can take any shape and can include any number of fittings. Shaft 120 includes primary region 120P having a diameter D1 and a reduced diameter region 120R having a diameter D2. Diameter D2 is less than diameter D1, with this change in diameter occurring at a transition region 120T.

In various embodiments, shaft 120 can be formed from any material that can take the desired shaft shape, such as silicone, polyvinyl chloride, latex rubber, polyethylene, polyurethane, Nitinol, or stainless steel, among others. Note also that while transition region 120T is depicted as a conically tapering region from diameter D1 to diameter D2 for exemplary purposes, in various other embodiments, transition region 120T can take any shape, such as a step (or multi-step) transition or a curved transition.

A distal end region of inflatable structure 110 is coupled to reduced diameter region 120R, such that at least a portion of reduced diameter region 120R is enclosed within inflatable structure 110. For exemplary purposes, the proximal end region of inflatable structure 110 is shown coupled to primary region 120P of shaft 120, although in various other embodiments, the proximal end region of inflatable structure 110 can be coupled to reduced diameter region 120R and/or transition region 120T.

Inflatable structure 110 also encloses one or more inflation ports 125 that are in communication with an interior lumen 120L of shaft 120, thereby allowing inflation fluid (e.g., saline, contrast solution, or air, among others) to be delivered to the interior of inflatable structure 110 via shaft 120. Such inflation fluid can be fed into shaft 120 via one or more fittings 141 on connector 140 (as described in greater detail below). Note that while two inflation ports 125 in reduced diameter region 120R are depicted for exemplary purposes, IBT 100 can include any number of inflation ports 125 of any shape (e.g., round or slot-shaped, among others), size(s), and/or location (e.g., in reduced diameter region 120R, transition region 120R, and/or primary region 120P).

Inflatable structure 110 can be formed from any type of inflatable material, including non-compliant materials (e.g., many Nylon and polyethylene materials), semicompliant materials (e.g., many polyurethane materials), compliant materials (e.g., latex rubber), or any combination thereof. Inflatable structure 110 can also have any size/shape. While a dual-lobed ("peanut shaped") configuration s depicted for exemplary purposes, in various other embodiments, inflatable structure 110 can be ovoid, spheroid, cylindrical, or any other shape.

In some embodiments, an optional stiffening stylet 130 (e.g., stainless steel, Nitinol, or any other supportive material) can be removably or permanently inserted into lumen 120L of shaft 120 to provide some additional rigidity to reduced diameter region 120R and/or inflatable structure 110 (for example, to assist with placement, inflation, and/or removal of inflatable bone tamp 100 during a surgical procedure). In various embodiments, stylet 130 can include a cap or cover 130C for securing and sealing to connector 140 (e.g., via a threaded or locking interface).

Note that typically, the distal end of reduced diameter region 120R is closed off to prevent unwanted material ingress into lumen 120L and to enable high pressure inflation of inflatable structure 110. However, in various embodiments, optional stiffening stylet 130 can be used to seal the distal end of reduced diameter region 120R (e.g., the diameter of stylet 130 can be the same as or slightly larger than the inner diameter of reduced diameter region 120R, or stylet 130 can include one or more features to engage with and seal off reduced diameter region 120R), thereby allowing lumen 120L to be used for non-inflation operations as well (e.g., aspiration or irrigation).

In another embodiment, one or more radiopaque markers 120M can be placed at one or more locations on inflatable bone tamp 100 to assist in visualization of inflatable bone tamp 100 during a surgical procedure. Note that although a single marker 120M positioned at the proximal end region of reduced diameter region 120R is shown for exemplary purposes, in various other embodiments, markers 120M can additionally or alternatively be placed at any number of locations on inflatable bone tamp 100. In various other embodiments, some or all of shaft 120 and/or some or all of inflatable structure 110 can be formed from or can incorporate radiopaque materials, markings, or structures.

Figure 1B:
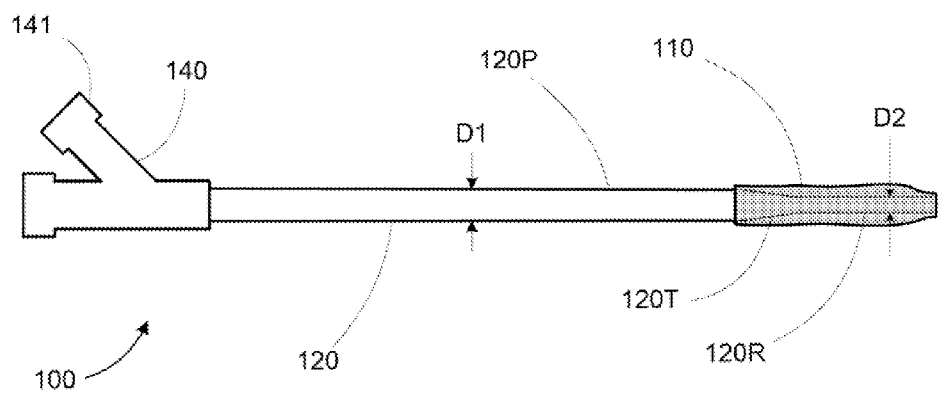

FIG. 1B shows inflatable bone tamp 100 with inflatable structure 110 fully deflated around reduced diameter region 120R of shaft 120. Reduced diameter region 120S beneficially allows inflatable structure 110 to have a more compact deflated profile than would be possible if inflatable structure 110 were mounted solely upon primary region 120P and its larger diameter D1. This in turn allows inflatable bone tamp 100 to be more readily maneuvered and delivered through a smaller cannula, thereby beneficially enhancing the suitability of inflatable bone tamp 100 for use in minimally invasive surgical procedures.

Figure 2:
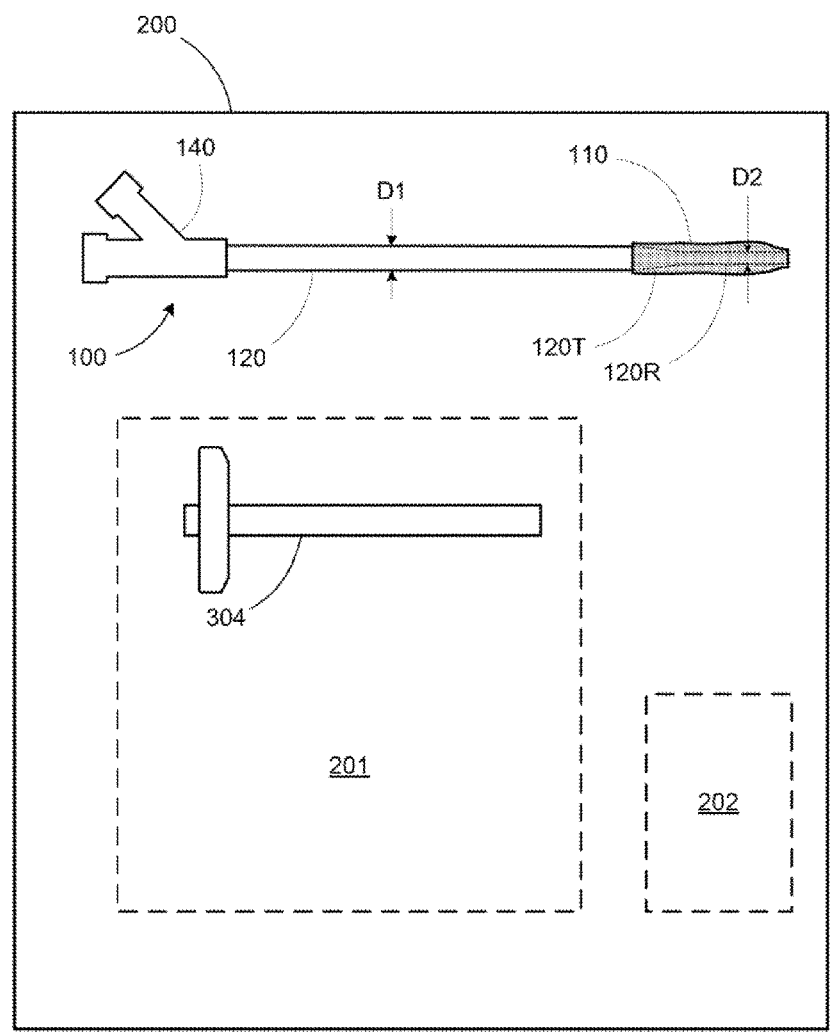
FIG. 2 shows a kit that includes the inflatable bone tamp of FIGS. 1A-1B.

FIG. 2 shows a diagram of a kit 200 for use in performing a surgical procedure (e.g., a kyphoplasty procedure described with respect to FIGS. 3A-3G below). Kit 200 includes an inflatable bone tamp 100 (as described above with respect to FIGS. 1A-1B) that incorporates an inflatable structure 110 mounted at least partially about a reduced diameter region 120R of a shaft 120. In various embodiments, kit 200 can further include, optional additional instruments 201, such as a cannula 204 sized to receive inflatable bone tamp 100, an introducer, guide pin, drill, curette, and/or access needle, among others (only cannula 204 is shown for clarity). In various other embodiments, kit 200 can further include optional directions for use 202 that provide instructions for using inflatable bone tamp 100 and optional additional instruments 201 (e.g., instructions, for performing a kyphoplasty procedure using inflatable bone tamp 100 and optional additional instruments 201).

Figure 3A:
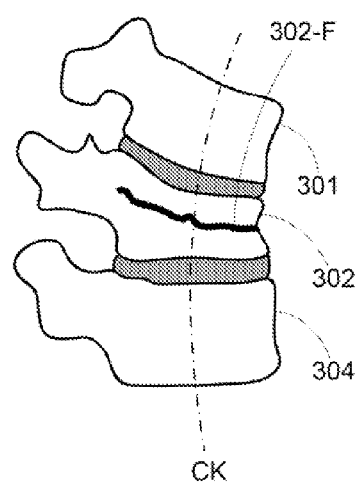
FIGS. 3A-3G show an exemplary kyphoplasty procedure using the inflatable bone tamp of FIGS. 1A-1B.

FIGS. 3A-3G show an exemplary kyphoplasty procedure using an inflatable bone tamp 100 as described with respect to FIGS. 1A-1B above. FIG. 3A shows a portion of a human vertebral column having vertebrae 301, 302, and 303. Vertebra 302 has collapsed due to a vertebral compression fracture (VCF) 302-F that could be the result of osteoporosis, cancer-related weakening of the bone, and/or physical trauma. The abnormal curvature CK of the spine caused by VCF 302-F can lead to severe pain and further fracturing of adjacent vertebral bodies.

Figure 3B:
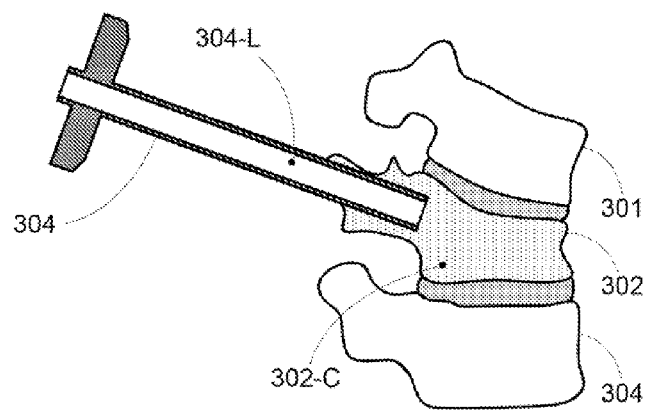

FIG. 3B shows a cannula 304 being positioned next to the target surgical location, which in this case is the cancellous bone structure 302-C within fractured vertebra 302. In this manner, a percutaneous path to vertebra 302 is provided via an interior lumen 304-L of cannula 304. Typically, cannula 304 is docked into the exterior wall of the vertebral body (using either a transpedicular or extrapedicular approach) using a guide needle and/or dissector, after which a drill or other access tool (not shown) is used to create a path further into the cancellous bone 302-C of vertebra 302. However, any other method of cannula placement can be used to position cannula 304.

Figure 3C:
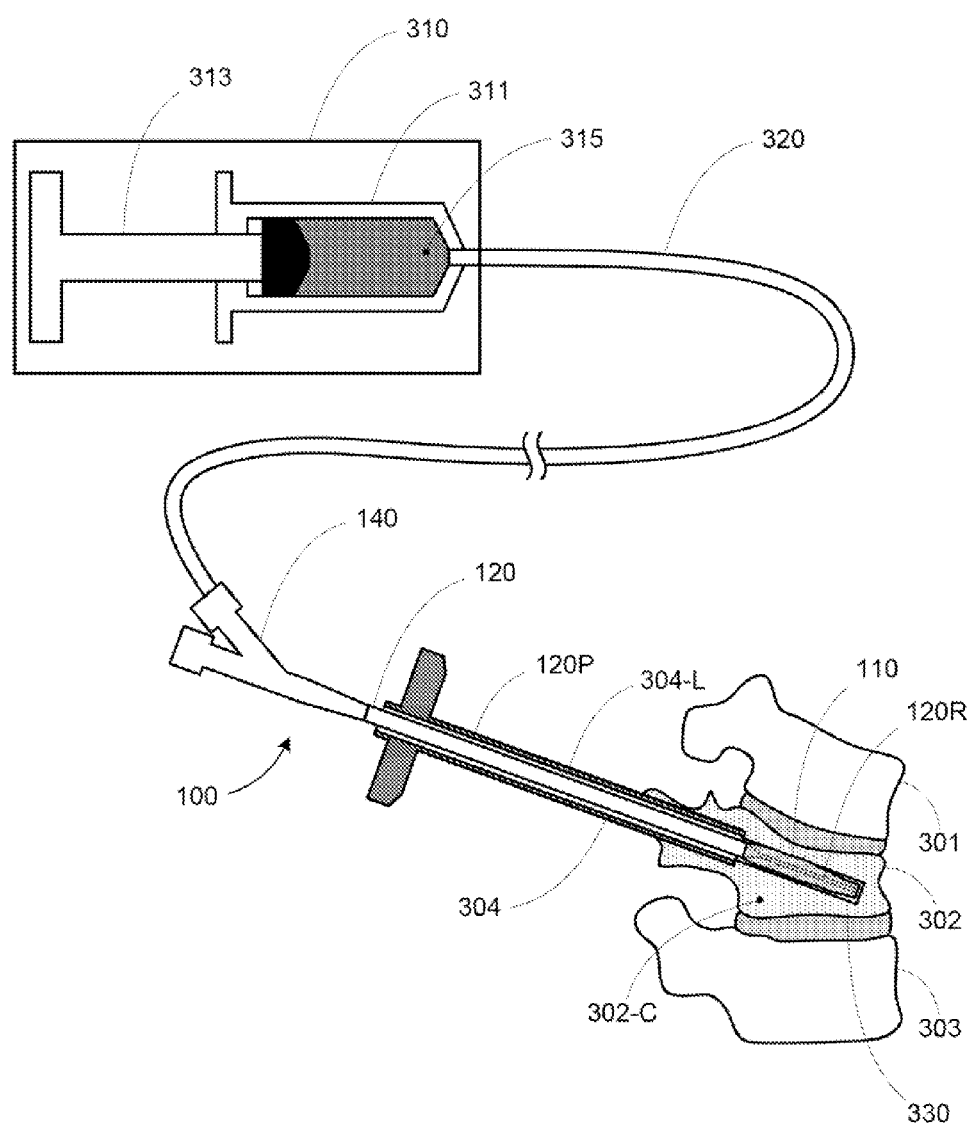

Then in FIG. 3C, an inflatable bone tamp 100 is placed into cannula 304. Inflatable bone tamp 100 includes a shaft 120 (e.g., a catheter), an inflatable structure 110 (e.g., a balloon) at the distal end of shaft 120, and a connector 140 (e.g., a Luer Lock fitting) at the proximal end of shaft 120. Inflatable bone tamp 100 is coupled to inflation mechanism 310 by a flow channel 320 (e.g., flexible tubing). For exemplary purposes, inflation mechanism 310 is depicted as a syringe having a plunger 313 for expressing inflation fluid 315 (e.g., saline solution, air, contrast solution, or any other fluid) from a barrel 311. Note that in various other embodiments, inflation mechanism 310 can be any system for delivering inflation, such as a syringe, pump, or compressed gas system, among others. Furthermore, in various other embodiments, inflation mechanism 310 can be directly connected to inflatable bone tamp 140.

Shaft 120 is used to position inflatable structure 110 at a desired location within cancellous bone 302-C. As noted above with respect to FIG. 1B, in some embodiments, inflatable bone tamp 100 can include one or more radiopaque markers, markings, or materials to facilitate this placement under remote visualization (e.g., fluoroscopic visualization). In some embodiments, inflatable structure 110 can be placed into a pre-formed channel or cavity 330 in cancellous bone 302-C (e.g., formed by a drill, obturator, or other instrument). In other embodiments, inflatable structure 110 can be used to form its own path within cancellous bone 302-C (e.g., due to inherent stiffness or in conjunction with a stiffening member, such as stylet 130 described above with respect to FIG. 1A).

As described above, inflatable structure 110 is mounted at least partially around a reduced diameter region 120R of shaft 120. Inflatable structure 110 can therefore assume a relatively compact deflated configuration about reduced diameter region 120R that can fit through the interior lumen 304-L of cannula 304. Reduced diameter region 120R thereby allows inflatable structure 110 to exhibit a larger maximum inflation volume than an inflatable structure mounted on the a similarly sized shaft 120 that does not include a reduced diameter region but still must fit through interior lumen 304-L of cannula 304.

Next, as shown in FIG. 2D, inflation mechanism 310 is actuated to drive inflation fluid 315 into inflatable structure 110, and inflatable structure 110 expands within fractured vertebra 302. For example, in the embodiment shown in FIG. 2D, a force is applied to drive plunger 313 through barrel 311, thereby expressing inflation fluid 315 through flow channel 320, connector 140, shaft 120, and into inflatable structure 110. The resulting expansion of inflatable structure 110 compresses the surrounding cancellous bone 302-C to create a cavity within vertebra 302.

In addition, as inflatable structure 110 performs this compression of cancellous bone 302-C, it approaches the harder endplates 302-E1 (inferior) and 302-E2 (superior) of vertebra 302. In many instances, the continued expansion of inflatable structure 110 can move endplates 302-E1 and 302-E2 apart, thereby providing beneficial height restoration of fractured vertebra 302.

Figure 3D:
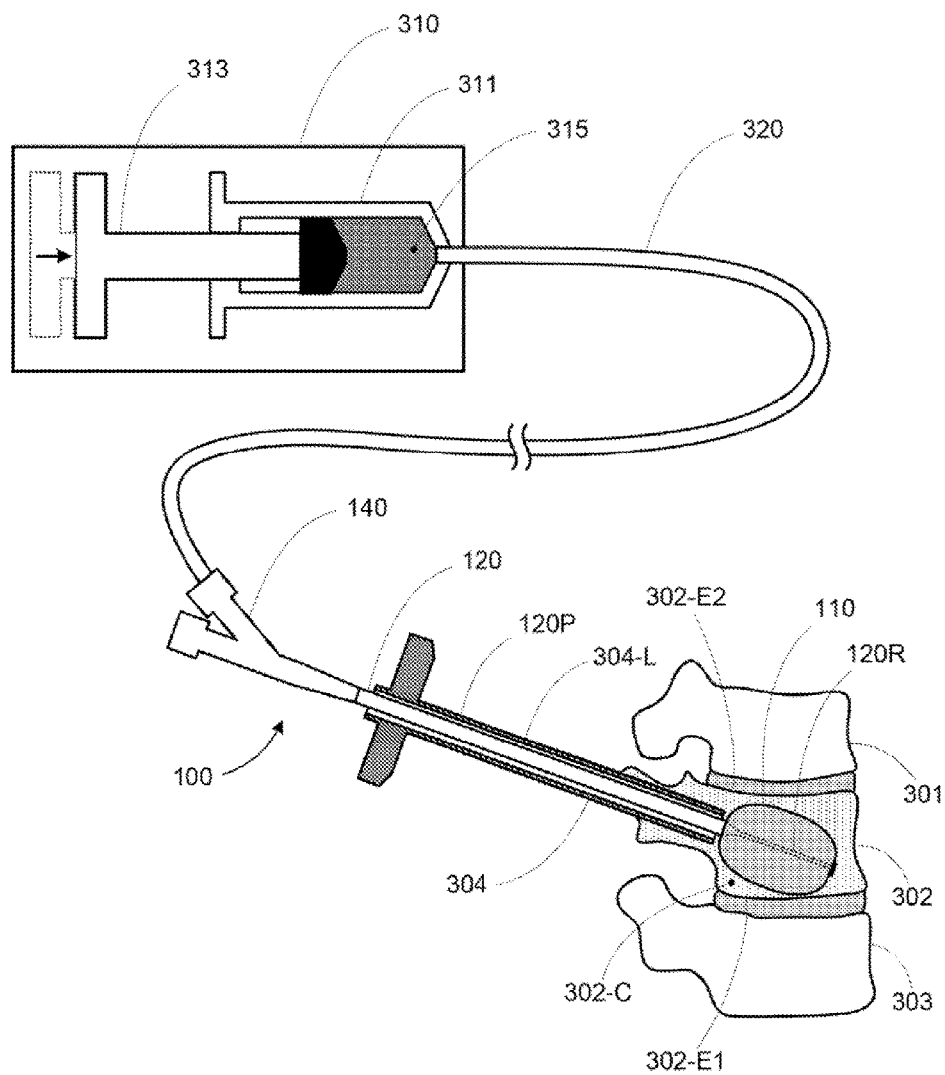
Figure 3E:
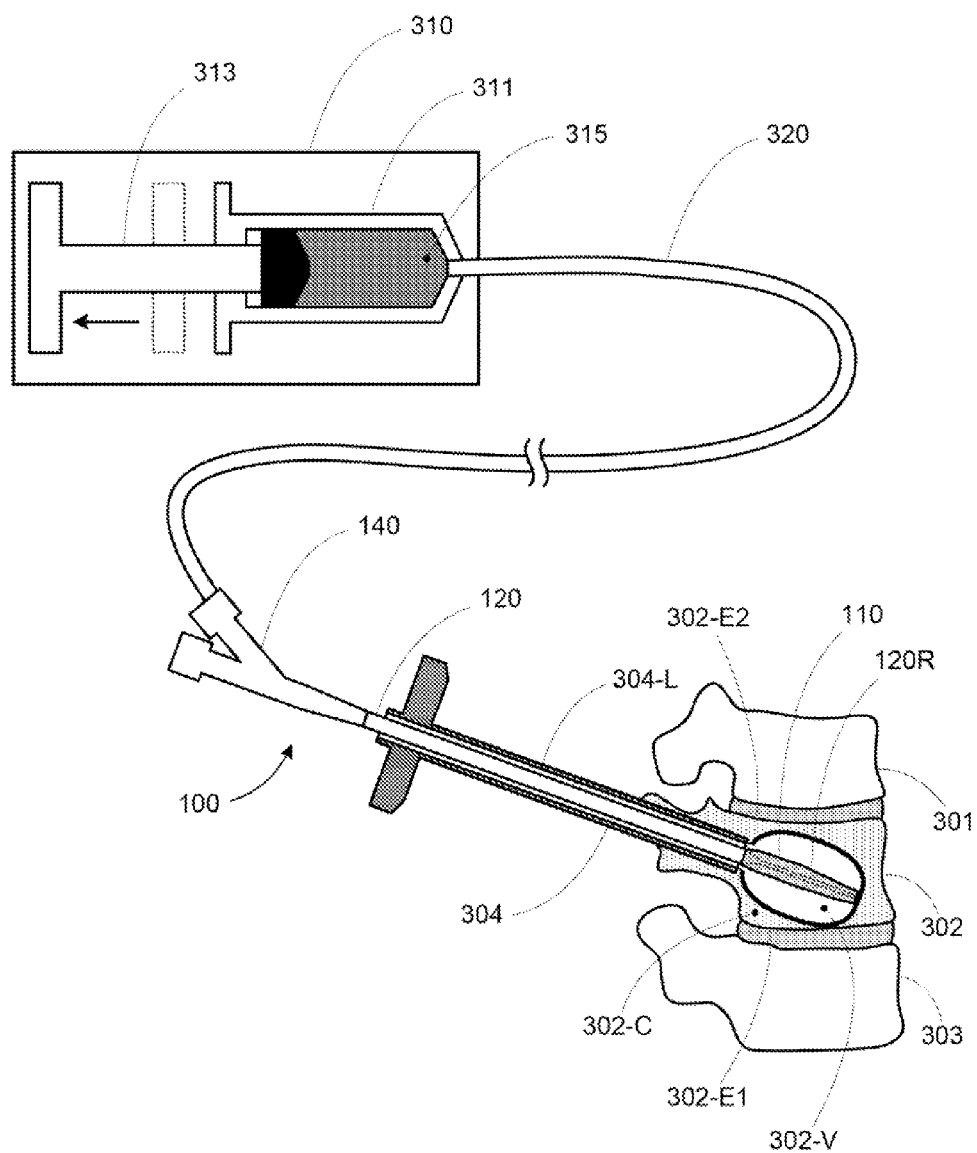

Once inflatable structure 110 has been expanded to a desired volume and/or a desired height restoration has been achieved in vertebra 302, inflatable structure 110 is deflated, as shown in FIG. 3E. The reduced diameter portion 120R of shaft 120 allows inflatable structure 110 to be compactly deflated, thereby facilitating the withdrawal of inflatable bone tamp 100 from cannula 304 through interior lumen 304-L.

Figure 3F:
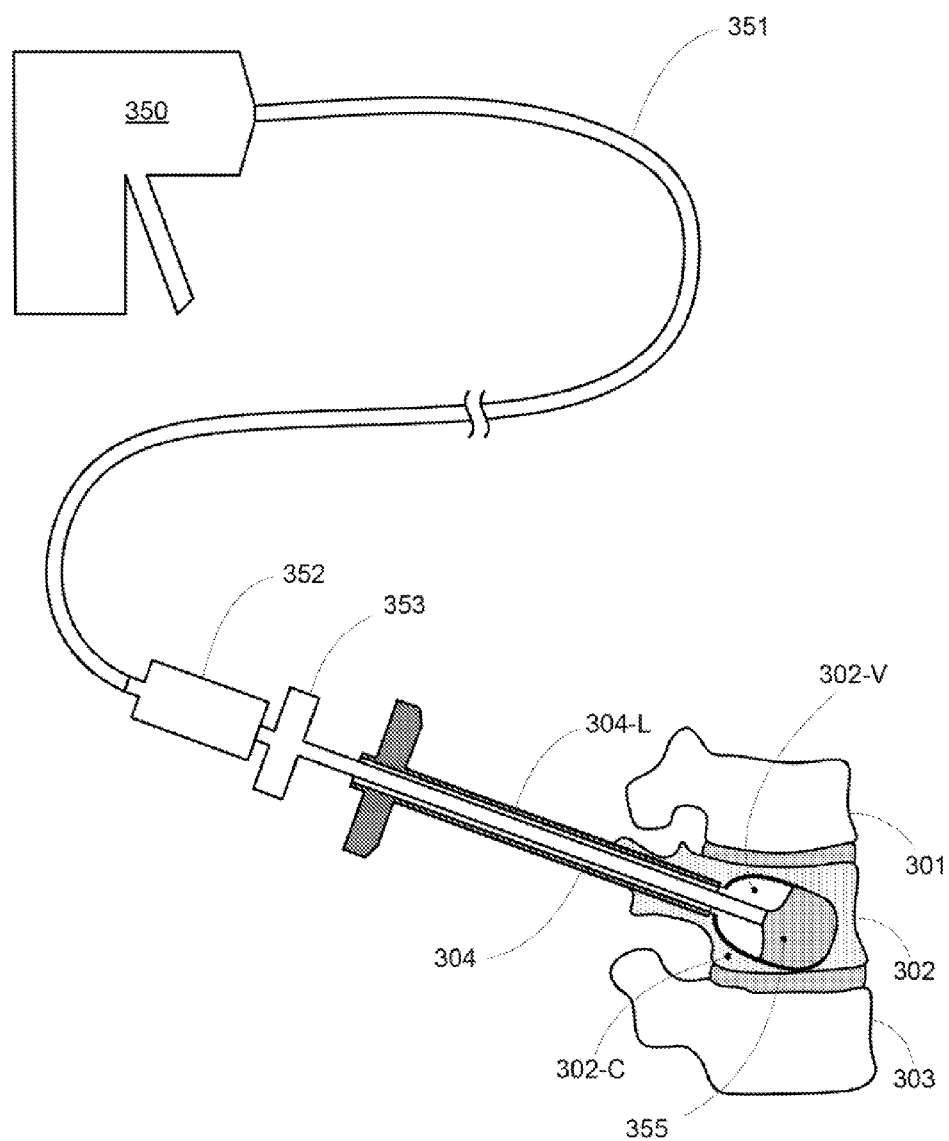

As shown in FIG. 3E, the result of the previously described expansion procedure is a well-defined cavity 302-V in cancellous bone 302-C, and a restoration of some or all of the original height of vertebra 302. Cavity 302-V can then be filled with bone filler material 255 (e.g., PMMA), as shown in FIG. 3F. A delivery nozzle 353 can be inserted through cannula 304 and into cavity 302-V, and can then be used to direct bone filler material 355 into cavity 302-V.

As shown in FIG. 3F, in one embodiment, a quantity of bone filler material 355 can be housed in a cartridge 352 attached to delivery nozzle 353. A hydraulic actuator 350 can then be used to remotely express bone filler material 355 from cartridge 352 via a hydraulic line 351 (e.g., cartridge 352 can include a piston that is driven by the hydraulic pressure supplied by hydraulic line 351). Note, however, that in various other embodiments, bone filler material 355 can be delivered to cavity 302-V in any number of different ways (e.g., a high pressure cement delivery pump that delivers the cement to nozzle 353 through a flexible line, or a syringe or other delivery device filled with bone filler material 355 that is attached directly to nozzle 353). In addition, in various other embodiments, bone filler material 355 can be delivered in multiple portions of the same or different materials (e.g., a bone cement followed by a biologic agent).

Figure 3G:
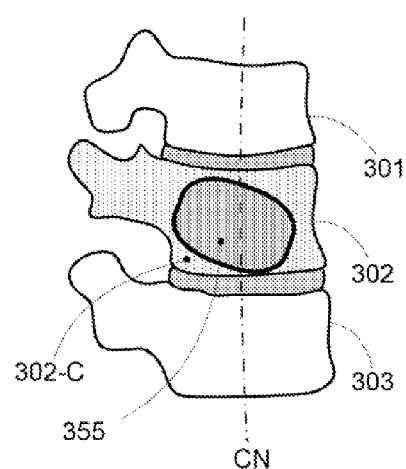

Once the filling operation is complete, delivery nozzle 353 and cannula 304 are removed from vertebra 302 (and the patients body) as shown in FIG. 3G. Upon hardening, bone filler material 355 provides structural support for vertebra 302, thereby substantially restoring the structural integrity of the bone and the proper musculoskeletal alignment of the spine. As shown in FIG. 3G, due to the restoration of height in fractured vertebra 302, the abnormal curvature CK shown in FIG. 3A is corrected to a normal curvature CN. In this manner, the pain and attendant side effects of a vertebral compression fracture can be addressed by a minimally invasive kyphoplasty procedure.

Note that although a kyphoplasty procedure is depicted and described for exemplary purposes, inflatable bone tamp 100 can be similarly used in any other target surgical location in or around bone, such as a tibial plateau fracture, a proximal humerus fracture, a distal radius fracture, a calcaneus fracture, a femoral head fracture, among others. Various other usages will be readily apparent.

Figure 4:
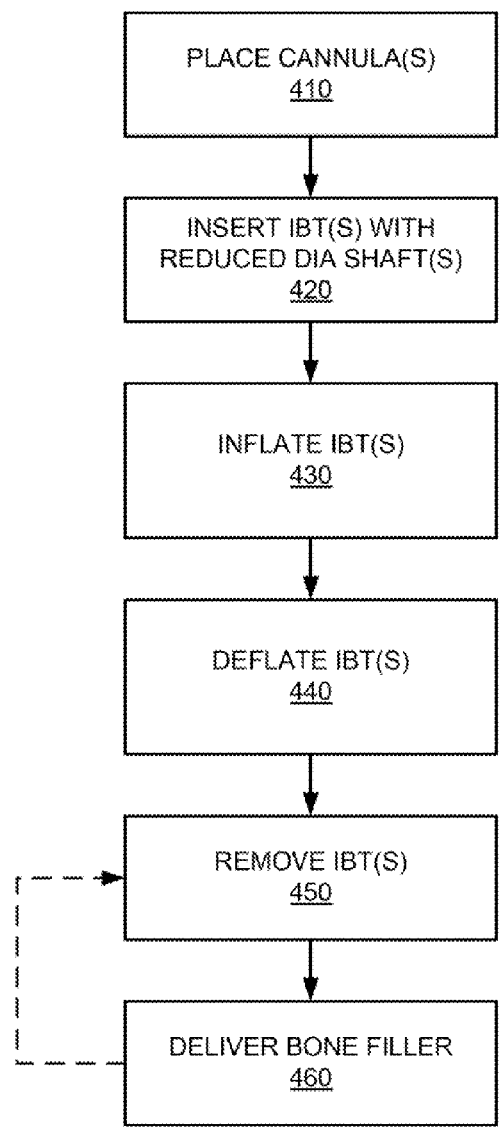
FIG. 4 shows a flow diagram for an exemplary surgical procedure using the inflatable bone tamp of FIGS. 1A-1B.

FIG. 4 shows a flow diagram of a process for performing a surgical procedure such as kyphoplasty using an inflatable bone tamp incorporating a shaft having a reduced diameter region. In a PLACE CANNULA(S) step 410, a cannula is positioned within a patient to provide a path to a target surgical location (e.g., as described with respect to FIG. 3B). Note that although a unilateral procedure is described above for clarity, in various other embodiments, a bilateral procedure can be used (e.g., placing two cannulas to provide access through both pedicles of a vertebra).

Then, in an INSERT IBT(S) WITH REDUCED DIA SHAFT(S) step 420, an inflatable bone tamp having an inflatable structure at least partially surrounding a reduced diameter shaft region (e.g., as described with respect to FIGS. 1A-1B) is placed within the patient through the cannula (e.g., as described with respect to FIG. 3C). Note once again that if multiple cannulas have been placed in step 410, an inflatable bone tamp can be inserted into each cannula (with at least one of the inflatable bone tamps exhibiting a shaft having a reduced diameter region for the inflatable structure).

Next, in an INFLATE IBT(S) step 430, the inflatable bone tamp(s) is (are) inflated to create a cavity(ies) in cancellous bone and, ideally at least partially restore the original cortical bone profile (e.g., as described with respect to FIGS. 3D and 3E). Note that if multiple inflatable bone tamps have been introduced in step 420, their inflation can be sequential, simultaneous, sequentially incremental (e.g., partially inflating one before partially or fully inflating another), or any other order.

The inflatable bone tamps) is (are) then deflated in a DEFLATE IBT(S) step 440 (e.g., as described with respect to FIG. 3E) and withdrawn from the patient in a REMOVE IBT(S) step 450 (e.g., as described with respect to FIG. 3F), and in a DELIVER BONE FILLER step 460, a bone filler material (e.g., bone cement) is conveyed to the cavity formed by the inflatable bone tamp to create a permanent reinforcing structure within the bone (e.g., as described with respect to FIGS. 3F and 3G).

Note that if multiple bone tamps have been placed within the patient (e.g., in a bilateral procedure) in step 420, one or more of those inflatable bone tamps can be left (inflated) within the patient to provide support for the bone structure during subsequent material delivery during step 460. The process can then loop back to step 440 and then step 450 until all inflatable bone tamps have been removed, and all the resulting cavities in the bone have been filled with bone filler material.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The invention claimed is:

1. A surgical device comprising:
    a shaft comprising an inner surface defining a lumen, the shaft extending along a longitudinal axis between a proximal end and a distal end comprising a primary region having a first diameter, a secondary region having a reduced second diameter and a transition region that is tapered continuously from the primary region to the secondary region;
    a balloon comprising a proximal end that is coupled to the primary region and a distal end that is coupled to the secondary region; and
    a stylet comprising a rod that is movably positioned within the lumen, the rod having a maximum outer diameter that is equal to or greater than a maximum inner diameter of the secondary region, the stylet being movable between a first configuration in which the rod is spaced apart from the inner surface and a second configuration in which rod engages the inner surface to seal the secondary region,
    wherein the secondary region comprises a port that is in communication with the lumen and a chamber of the balloon such that an inflation material may be moved through the lumen and into the chamber through the port when the stylet is in the first configuration to increase a volume of the chamber.

2. A surgical device as recited in claim 1, wherein the surgical device is configured to prevent the inflation material from moving into the lumen through the port when the stylet is in the second configuration.

3. A surgical device as recited in claim 1, wherein the stylet further includes at least one feature that engages the inner surface to seal off the secondary region when the stylet is in the second configuration.

4. A surgical device as recited in claim 1, wherein the maximum outer diameter of the rod is equal to the maximum inner diameter of the secondary region.

5. A surgical device as recited in claim 1, wherein the maximum outer diameter of the rod is greater than the maximum inner diameter of the secondary region.

6. A surgical device as recited in claim 1, wherein the shaft has a smooth outer surface along an entire length of the shaft.

7. A surgical device as recited in claim 1, wherein the port includes two spaced apart ports on one side of the shaft.

8. A surgical device as recited in claim 1, wherein the port comprises a plurality of ports that are spaced apart from one another.

9. A surgical device as recited in claim 1, wherein the rod comprises nitinol.

10. A surgical device as recited in claim 1, further comprising a connector coupled to the primary region, the rod extending through the connector, the stylet further comprising a cap that is coupled to the rod, the cap having threads that engage threads on the connector to secure and seal the stylet to the connector.

11. A surgical device as recited in claim 1, wherein when inflated, a proximal half of the balloon has a maximum interior volume that is less than that of a distal half of the balloon, the proximal half of the balloon having a maximum radial diameter that is less than that of the distal half of the balloon when the balloon is inflated.

12. A surgical device as recited in claim 1, wherein when inflated, the balloon has a dual-lobed, peanut shaped configuration comprising a proximal lobe and a distal lobe, the distal lobe having a larger maximum radial diameter than the proximal lobe upon inflation of the balloon.

13. A surgical device as recited in claim 1, wherein an inner diameter of the secondary region remains constant along an entire length of the secondary region as the stylet moves between the first and second configurations.

14. A surgical device as recited in claim 1, wherein an outer diameter of the secondary region remains constant along an entire length of the secondary region as the stylet moves between the first and second configurations.

15. A kit comprising: the surgical device recited in claim 1;
a cannula sized to receive the surgical device; and instructions for use.

16. A method comprising:
providing the surgical device recited in claim 1;
establishing an access path to a bone;
moving the shaft through the access path until the distal end of the balloon is positioned adjacent to the bone;
moving the rod through the lumen such that the stylet is in the first configuration;
moving the rod through the lumen such that the stylet moves from the first configuration to the second configuration; and
inflating the balloon when the stylet is in the first configuration to manipulate the bone.

17. A method as recited in claim 16, further comprising moving a material through the lumen and out of an opening in the distal end of the shaft when the stylet is in the first configuration such that the material irrigates the bone.

18. A method as recited in claim 16, further comprising aspirating a material adjacent to the bone such that the material moves through an opening in the distal end of the shaft and into the lumen when the stylet is in the first configuration.

19. A surgical device comprising:
a shaft comprising an inner surface defining a lumen, the shaft extending along a longitudinal axis between a proximal end and a distal end comprising a primary region having a first diameter and a secondary region having a reduced second diameter;
a connector coupled to the primary region;
a balloon comprising a proximal end that is coupled to the primary region and a distal end that is coupled to the secondary region; and
a stylet comprising a cap and a rod that extends from the cap, the cap having threads that engage threads on the connector to secure the stylet to the connector, the rod being movably positioned within the lumen, the rod having a maximum outer diameter that is equal to or greater than a maximum inner diameter of the secondary region, the stylet being movable between a first configuration in which the rod is spaced apart from the inner surface and a second configuration in which the rod engages the inner surface to seal a distal end of the secondary region,
wherein the surgical device is configured to allow material in the lumen to move into a chamber of the balloon when the stylet is in the first configuration,
and wherein the stylet is configured to prevent material in the lumen from moving into the chamber when the stylet is in the second configuration.

20. A surgical device comprising:
a shaft comprising an inner surface defining a lumen, the shaft extending along a longitudinal axis between a proximal end and a distal end comprising a primary region having a uniform first diameter, a secondary region having a reduced uniform second diameter and a transition region that is tapered continuously from the primary region to the secondary region;
a connector coupled to the primary region;
a balloon comprising a proximal end that is coupled to the primary region and a distal end that is coupled to the secondary region; and
a stylet comprising a cap and a rod that extends from the cap, the cap having threads that engage threads on the connector to secure the stylet to the connector, the rod being movably positioned within the lumen, the rod having a maximum outer diameter that is equal to or greater than a maximum inner diameter of the secondary region, the stylet being movable between a first configuration in which the rod is spaced apart from the inner surface and a second configuration in which the rod engages the inner surface to seal a distal end of the secondary region,
wherein when the stylet is in the first configuration, the lumen is in communication with a chamber of the balloon, and
wherein when the stylet is in the second configuration, the lumen is not in communication with the chamber.

* * * * *